(12) United States Patent
Cha et al.

(10) Patent No.: US 12,171,886 B2
(45) Date of Patent: *Dec. 24, 2024

(54) MUSSEL ADHESIVE PROTEIN-BASED PHOTOTHERMAL AGENT AND PHOTOTHERMAL-RESPONSIVE ADHESIVE NANOPARTICLES

(71) Applicant: POSTECH RESEARCH AND BUSINESS DEVELOPMENT FOUNDATION, Pohang-si (KR)

(72) Inventors: Hyung Joon Cha, Pohang-si (KR); Yeon Su Jeong, Nam-gu (KR); Yun Kee Jo, Ansan-si (KR); Kye Il Joo, Daegu (KR)

(73) Assignee: POSTECH RESEARCH AND BUSINESS DEVELOPMENT FOUNDATION, Pohang-si (KR)

( * ) Notice: Subject to any disclaimer, the term of this patent is extended or adjusted under 35 U.S.C. 154(b) by 776 days.

This patent is subject to a terminal disclaimer.

(21) Appl. No.: 17/416,685

(22) PCT Filed: Dec. 4, 2019

(86) PCT No.: PCT/KR2019/016994
§ 371 (c)(1),
(2) Date: Jun. 21, 2021

(87) PCT Pub. No.: WO2020/130428
PCT Pub. Date: Jun. 25, 2020

(65) Prior Publication Data
US 2022/0071918 A1 Mar. 10, 2022

(30) Foreign Application Priority Data
Dec. 21, 2018 (KR) .................. 10-2018-0167754

(51) Int. Cl.
| A61K 9/51 | (2006.01) |
| A61K 31/70 | (2006.01) |
| A61K 41/00 | (2020.01) |
| A61K 31/7048 | (2006.01) |

(52) U.S. Cl.
CPC .......... *A61K 9/5169* (2013.01); *A61K 9/5115* (2013.01); *A61K 9/5123* (2013.01); *A61K 9/5192* (2013.01); *A61K 41/0052* (2013.01); *A61K 31/7048* (2013.01)

(58) Field of Classification Search
CPC .............. A61K 9/5169; A61K 41/0052; A61K 31/7048
See application file for complete search history.

(56) References Cited

U.S. PATENT DOCUMENTS

| 8,173,395 | B2 * | 5/2012 | Cha | C07K 14/43504 |
| | | | | 435/348 |
| 8,673,986 | B2 * | 3/2014 | Cha | A61P 35/00 |
| | | | | 514/772.1 |
| 8,765,682 | B2 * | 7/2014 | Cha | C07K 14/43504 |
| | | | | 435/348 |
| 9,005,992 | B2 * | 4/2015 | Cha | G01N 33/54353 |
| | | | | 436/518 |
| 9,675,629 | B2 * | 6/2017 | Cha | A61K 9/1658 |
| 9,801,972 | B2 * | 10/2017 | Cha | A61L 27/30 |
| 11,267,851 | B2 * | 3/2022 | Cha | A61K 9/5169 |
| 11,814,556 | B2 * | 11/2023 | Cha | A61L 24/10 |
| 2008/0154101 | A1 * | 6/2008 | Jain | A61B 5/076 |
| | | | | 600/309 |
| 2016/0263136 | A1 * | 9/2016 | Cha | A61K 9/1617 |
| 2017/0190746 | A1 * | 7/2017 | Cha | A61L 24/0015 |

FOREIGN PATENT DOCUMENTS

| BR | 102012016127 A2 * | 9/2015 |
| KR | 10-2014-0027031 | 3/2014 |
| KR | 10-2016-0026441 | 3/2016 |
| KR | 10-2016-0110864 | 9/2016 |
| KR | 10-2016-0129982 | 11/2016 |
| WO | 2005-092920 | 10/2005 |
| WO | 2006-107183 | 10/2006 |
| WO | WO-2009001220 A2 * | 12/2008 | ............. C23C 16/34 |

OTHER PUBLICATIONS

Zeng, Hongbo, et al. "Strong reversible Fe3+-mediated bridging between dopa-containing protein films in water." Proceedings of the National Academy of Sciences 107.29 (2010): 12850-12853.

Fan, Jing, et al. "Light-responsive biodegradable nanomedicine overcomes multidrug resistance via NO-enhanced chemosensitization." ACS applied materials & interfaces 8.22 (2016): 13804-13811, May 23, 2016.

Kao, Po-Tsung, et al. "Controllable NO release from Cu 1.6 S nanoparticle decomposition of S-nitrosoglutathiones following photothermal disintegration of polymersomes to elicit cerebral vasodilatory activity." Chemical science 8.1 (2017): 291-297.

Jeong, Yeonsu, et al. "Sprayable adhesive nanotherapeutics: mussel-protein-based nanoparticles for highly efficient locoregional cancer therapy." ACS nano 12.9 (2018): 8909-8919.

Yeonsu Jeong et al., "Mussel Protein-Based Photo-Activated Nanosystem for Synergistic Cancer Therapy", 2019 Spring Meeting the KSBM(Mar. 28, 2019) (abstract only).

(Continued)

*Primary Examiner* — Amber D Steele

(74) *Attorney, Agent, or Firm* — LEX IP MEISTER, PLLC

(57) ABSTRACT

The present invention relates to: a photothermal agent which includes a mussel adhesive protein; and photothermal-responsive nanoparticles that generate a biocompatible gas by means of light and heat and release a drug. Nanoparticles according to the present invention exhibit a photothermal effect when near-infrared rays are applied thereto, and may be applied to trimodality therapy in which a biocompatible gas is generated by means of light and heat to induce the release of a drug.

4 Claims, 6 Drawing Sheets

Specification includes a Sequence Listing.

(56) References Cited

OTHER PUBLICATIONS

Yeonsu Jeong et al., "Photothermal-activated mussel adhesive protein nanoparticles for synergistic cancer therapy", 2019 KSBB Spring Meeting and International Symposium(Apr. 10, 2019) (abstract only).

Y. Jeong et al., "Mussel protein nanoparticle-mediated photo-responsive system for cancer-specific photothermal-chemotherapy", TERMIS EU 2019, May 27-31, 2019, Rhodes, Greece.

Y. Jeong et al., "Bioinspired Protein-Based Laser-Activated Nanotherapy for Synergistic Cancer Treatment", TERMIS-AP 2019(Oct. 14, 2019).

* cited by examiner

MUSSEL ADHESIVE PROTEIN-BASED PHOTOTHERMAL AGENT AND PHOTOTHERMAL-RESPONSIVE ADHESIVE NANOPARTICLES

TECHNICAL FIELD

The present invention relates to a mussel adhesive protein-based photothermal agent and photothermal-responsive adhesive nanoparticles.

BACKGROUND ART

Many studies have been conducted on nanoparticles with a stimuli-responsive system that selectively releases the drug from the action region to efficiently deliver a drug to a particular therapy region in the drug delivery system. There is a system in which the drug is released in response to intracellular stimuli such as oxidation-reduction potential, pH, and specific enzymes, or external stimuli such as light, temperature, and magnetic fields, and the external stimuli have advantages of enabling the release of the drug to be controlled locally only in a specific region through remote equipment. Particularly, a photothermal-responsive system, as a system releasing the drug according as nanoparticles are broken or swollen due to heat generated when light is applied to the specific region, can increase the drug delivery efficiency and can reduce side effects of the drug in other regions by inducing or stopping drug release in the specific region, thereby enabling space-time to be controlled.

A system which not only carries out the therapy by drug delivery, but also can maximize the anti-cancer effect using a photothermal effect at the same time has recently been developed. As a photothermal therapy, as a therapy method of locally annihilating cancer cells using a photothermal agent converting light energy into thermal energy, is non-invasive, and can reduce side effects generated during chemotherapy, the development of photothermal agents for effective photothermal therapy and the research on photothermal agent delivery vehicles have actively been carried out. Since light in the near-infrared (NIR) region mainly has a high in vivo transmittance, photothermal agents that generate heat in response to near-infrared rays are preferred, and gold nanoparticles, carbon nanoparticles, or nanoparticles based on a polymer such as polypyrrole or polyaniline have mainly been studied a lot. However, the photothermal agents may not be decomposed or discharged from the body, there may be a risk of toxicity due to this, or the photothermal agents have various limitations by having low photothermal conversion efficiency, thereby making it difficult to obtain a sufficient photothermal therapy effect. Accordingly, it is necessary to develop photothermal agents which are excellent in biocompatibility, and not only have biodegradability, but also have high photothermal conversion efficiency.

Although the photothermal therapy has an effective anti-cancer effect, there is a limit to the complete removal of cancer due to the uneven heat distribution within cancer tissues and the complex microenvironment of cancer with various pathological pathways. Therefore, researches on the complex therapy that combines photothermal therapy with a therapy method showing the anti-cancer effect with other mechanisms to enhance the therapy effect have actively been conducted. Among the researches, a biocompatible gas transfer system using gas with excellent diffusivity to complement the limitations of the uneven heat distribution has been used a lot along with the photothermal therapy. Particularly, as a nitric oxide (NO) gas may induce the annihilation of cells and increase the sensitivity of cancer cells to chemicals, the NO gas has been used for anticancer therapy. However, the NO gas has limitations that, when injecting the gas itself into the body, the gas is diffused so that it easily leaves the desired region, the gas has a short half-life in the body, and it is difficult to deliver the gas to a target region. Therefore, to increase the stability and the tissue permeability of the gas, a carrier that can generate the gas in the body is needed.

As mussel adhesive protein (MAP) not only has excellent underwater adhesion, but also has excellent biocompatibility and biodegradability, the MAP has been studied a lot as a medical biomaterial. Surface adhesion of the MAP is enabled as the MAP forms a hydrogen bond or a covalent bond with nucleophile groups such as an amine group, a thiol group, a hydroxy group, etc. of the tissue surface through 3,4-dihydroxyphenylalanine (DOPA) residues existing in the mussel adhesive protein (MAP). Further, the DOPA residues combine with metal to form a metal-catechol complex, and the metal-catechol complex has been known to give excellent mechanical properties of mussel byssus as it is as strong as a covalent bond. Nanoparticles (NPs) with adhesive property can be synthesized using these characteristics, and, since mussel adhesive protein nanoparticles (MAP NPs) can be used as a drug carrier, a case of utilizing the MAP NPs as a local drug delivery system has been reported.

However, attempts of applying the MAP NPs themselves as a photothermal agent, or applying the MAP NPs to photothermal-responsive trimodality therapy based on this have not been made up to now.

DISCLOSURE

Technical Problem

An object of the present invention is to provide nanoparticles including a mussel adhesive protein, A, and $MX_3$, in which A is one selected from the group consisting of S-nitrosoglutathione, N,N'-di-sec-butyl-N,N'-dinitroso-1,4-phenylenediamine, Roussin's black salt, and S-nitrosothiol (SNO), M is Fe or V, and X is F, Cl, Br, or I.

Furthermore, an object of the present invention is to provide a pharmaceutical composition for preventing or treating cancer, including the nanoparticles.

Furthermore, an object of the present invention is to provide a preparation method of nanoparticles, including: a step 1) of mixing the mussel adhesive protein and $MX_3$, in which M is Fe or V, and X is F, Cl, Br, or I; and a step 2) of electrospraying a mixture of the step 1) to a rate of 0.5 to 1.5 ml/h and a voltage of 5 to 15 kV.

Furthermore, an object of the present invention is to provide nanoparticles prepared by the preparation method.

Technical Solution

One aspect of the present invention for achieving the foregoing object is to provide nanoparticles including a mussel adhesive protein, A, and $MX_3$, in which A is one selected from the group consisting of S-nitrosoglutathione, N,N'-di-sec-butyl-N,N'-dinitroso-1,4-phenylenediamine, Roussin's black salt, and S-nitrosothiol (SNO), M is Fe or V, and X is F, Cl, Br, or I.

The A may be a photothermal-responsive gas donor.

Although the A, i.e., the photothermal-responsive gas donor, as a material that generates a gas in response to light and heat, may be preferably S-nitrosoglutathione (GSNO), N,N'-di-sec-butyl-N,N'-dinitroso-1,4-phenylenediamine (BNN6), Roussin's black salt (RBS, $[NH_4][Fe_4S_3(NO)_7]$), and S-nitrosothiol (SNO) which generate a nitric oxide (NO) gas, perfluorinated carbon compounds (PFC) in liquid phase which generate oxygen, manganese carbonyl (MnCO) and ruthenium carbonyl cluster (Ru—CO) which generate carbon monoxide, perfluorohexane (PFH) which generates PFC, ammonium bicarbonate (ABC) or perfluoropentane (perfluorinated carbon compound (PFP)) which generates carbon dioxide, or the like, A is not limited thereto.

Although the gas, as a gas that has anti-cancer effects or is free from in vivo toxicity, may be preferably nitric oxide (NO), oxygen ($O_2$), hydrogen ($H_2$), carbon monoxide (CO), hydrogen sulfide ($H_2S$), sulfur dioxide ($SO_2$), carbon dioxide ($CO_2$), DL-menthol (DLM), perfluoropentane (PFP) in gas phase, perfluorocarbon (PFC), or the like, the gas is not limited thereto.

In the present invention, although the mussel adhesive protein, as a mussel-derived adhesive protein, may include preferably mussel adhesive proteins derived from *Mytilus edulis, Mytilus galloprovincialis* or *Mytilus coruscus*, or variants thereof, the mussel adhesive protein is not limited thereto.

Although a mussel adhesive protein according to the present invention may include Mefp (*Mytilus edulis* foot protein)-1, Mgfp (*Mytilus galloprovincialis* foot protein)-1, Mcfp (*Mytilus coruscus* foot protein)-1, Mefp-2, Mefp-3, Mgfp-3 and Mgfp-5 which are each derived from the above-mentioned mussel species, or variants thereof, preferably a protein selected from the group consisting of fp (foot protein)-1 (SEQ ID NO: 1), fp-2 (SEQ ID NO: 4), fp-3 (SEQ ID NO: 5), fp-4 (SEQ ID NO: 6), fp-5 (SEQ ID NO: 7), and fp-6 (SEQ ID NO: 8), a fusion protein to which two or more proteins are linked, or variants of the proteins, the mussel adhesive protein is not limited thereto. In addition, a mussel adhesive protein according to the present invention includes all mussel adhesive proteins described in International Publication No. WO2006/107183 or WO2005/092920. Although the mussel adhesive protein may include preferably fusion proteins such as fp-151 (SEQ ID NO: 9), fp-131 (SEQ ID NO: 10), fp-353 (SEQ ID NO: 11), fp-153 (SEQ ID NO: 12), fp-351 (SEQ ID NO: 13), etc., the mussel adhesive protein is not limited thereto. Further, a mussel adhesive protein according to the present invention may include a polypeptide in which a decapeptide (SEQ ID NO: 2) repeated about 80 times in fp-1 is continuously linked 1 to 12 times or more. Although the decapeptide represented by SEQ ID NO: 2 may be preferably an fp-1 variant polypeptide (SEQ ID NO: 3) which is continuously linked 12 times, it is not limited thereto.

Further, although a mussel adhesive protein according to the present invention may be a variant of fp-151 (SEQ ID NO: 15), the mussel adhesive protein is not limited thereto. A protein sequence represented by the SEQ ID NO: 15 is a sequence from which a linker sequence and the like are excluded compared to the SEQ ID NO: 9. Specifically, the protein sequence represented by the SEQ ID NO: 15 is a fusion protein sequence in which the sequence of Mgfp-5 represented by SEQ ID NO: 16 is fused between the fp-1 variant sequences represented by SEQ ID NO: 14.

In a preferred aspect of the present invention, a mussel adhesive protein according to the present invention includes an amino acid sequence represented by the SEQ ID NO: 1, SEQ ID NO: 9, or SEQ ID NO: 15.

Further, a mussel adhesive protein according to the present invention may be modified in a range including a conservative amino acid sequence capable of maintaining the properties of the mussel adhesive proteins mentioned above. That is, amino acid sequences having the sequence identity of 70% or more, preferably 80% or more, more preferably 90% or more, i.e., 95%, 96%, 97%, 98%, 99%, or more with amino acid sequences represented by the foregoing SEQ ID NOs exhibiting the substantially equivalent effect may also be included within the scope of the present invention.

It is preferable that 10 to 100% of the total tyrosine residues in the mussel adhesive protein is converted into DOPA, i.e., a catechol derivative. In most mussel-adhesive proteins, tyrosine accounts for about 20 to 30% of the total amino acid sequence. Tyrosine in natural mussel adhesive protein is converted into a DOPA form by adding —OH group through the hydration process. However, since tyrosine residues are not converted in a mussel adhesive protein produced from *E. coli*, it is preferable to perform a modified reaction in which tyrosine residues are converted into DOPA by a separate enzyme and chemical treatment method. A method of modifying tyrosine residues contained in the mussel adhesive protein into DOPA may use a method known to the art, and is not particularly limited. Preferably, tyrosine residues may be modified into DOPA residues using tyrosinase. In an example of the present invention, a mussel adhesive protein which satisfies the above-mentioned DOPA conversion rate may be produced through an in vitro enzyme reaction using mushroom tyrosinase.

The nanoparticles may be used as a photothermal agent using light in the near-infrared region.

In the present invention, the "photothermal agent" is a composition exhibiting a photothermal effect in the near-infrared region, and may be characterized by having excellent biocompatibility and biodegradability by including a mussel adhesive protein.

Particularly, the nanoparticles may be characterized by including a DOPA-metal complex. The metal capable of forming a complex with the DOPA may be a typical metal or a transition metal. For example, the metal may be titanium, iron, vanadium, manganese, cobalt, nickel, chrome, zirconium, ruthenium, rhodium, niobium, molybdenum, silver, gold, platinum, technetium, palladium, tungsten, osmium, iridium, rhenium, tantalum, hafnium, etc. which are capable of coordination bonding, and it is preferable that the metal is iron (III) or vanadium (III).

The nanoparticles may be characterized by further including an anti-cancer drug.

Although the anti-cancer drug may be one or more selected from the group consisting of an anthracycline-based anti-cancer drug, a taxane-based anti-cancer drug, an alkaloid-based anti-cancer drug, a vinca alkaloid-based anti-cancer drug, a platinum-based anti-cancer drug, antimetabolites, a topoisomerase inhibitor, antitumor antibiotics, an alkylating agent, a nucleoside analog, a genetic drug, an enzyme-based anti-cancer drug, and a hormone-based anti-cancer drug, the anti-cancer drug is not limited thereto.

Nonlimiting examples of the anti-cancer drug may be any one or more selected from the group consisting of doxorubicin, paclitaxel, azithromycin, erythromycin, vinblastine, bleomycin, dactinomycin, daunorubicin, idarubicin, mitoxantrone, plicamycin, and mitomycin, the nonlimiting examples of the anti-cancer drug are not limited thereto. A preferable example of the anti-cancer drug may be doxorubicin.

The nanoparticles are characterized by having biocompatibility. Further, the nanoparticles are characterized in that gas is generated by the photothermal effect. The nanoparticles may be those that release a gas which is harmless to a living body or has a therapeutic effect by a photothermal-responsive gas donor contained in the nanoparticles by the photothermal effect in the body. Although the gas is any one or more selected from the group consisting of nitric oxide, oxygen, hydrogen, carbon monoxide, hydrogen sulfide, sulfur dioxide, carbon dioxide, DL-menthol, and perfluorocarbon, it is not limited thereto.

The nanoparticles may have physical stability by bonding of DOPA and metal, and may have characteristics that the form of a DOPA-metal bond is changed into a mono-, bis-, or tris-form depending on the pH environment. In this case, pH conditions may vary depending on types of metal. Specifically, the nanoparticles have a mono-form at pH<5.5, a bis-form at 5.6<pH<9.1, and a tris-form at pH>9.1 when DOPA and iron have a molar ratio of 3:1 in case of a DOPA-iron bond, whereas the nanoparticles have a mono-form at pH<3, a his-form at 3<pH<8, and a tris-form at pH>8 when DOPA and vanadium have a molar ratio of 3:1 in case of a DOPA-vanadium bond. Further, the nanoparticles may have adhesive properties in the underwater environment through tyrosine residues or DOPA residues.

One aspect of the present invention for achieving the foregoing object is to provide a pharmaceutical composition for the prevention or treatment of cancer, including the nanoparticles.

Another aspect of the present invention for achieving the foregoing object is to provide a pharmaceutical composition for the prevention or treatment of cancer, including the nanoparticles as an active component.

The cancer may be any one or more selected from the group consisting of lung cancer, pancreatic cancer, colon cancer, colorectal cancer, myelogenous leukemia, thyroid cancer, myelodysplastic syndrome (MDS), bladder carcinoma, epidermic carcinoma, melanoma, breast cancer, prostate cancer, head and neck cancer, uterine cancer, ovarian cancer, brain cancer, stomach cancer, laryngeal cancer, esophagus cancer, bladder cancer, oral cavity cancer, cancer originated from hepatic lobes, sarcoma, teratocarcinoma, neuroblastoma, renal carcinoma, liver cancer, non-Hodgkin lymphomas, multiple myeloma, and undifferentiated thyroid cancer.

In the present invention, the term "prevention" means all acts of inhibiting cancer or delaying pathogenesis by the administration of the above-mentioned composition.

In the present invention, the term "treatment" means all acts of curing cancer by the administration of the composition, and is defined as application or administration of the composition including the nanoparticles to a subject (human or animal) having an illness, symptoms thereof, a secondary illness of a disease or illness, or a predisposition therefor along with the purposes of treating, alleviating, relieving, remedying, or improving an illness, symptoms thereof, a secondary illness of a disease or illness, or a predisposition therefor.

Although a pharmaceutical composition according to the present invention may include the nanoparticles in an amount of 0.0001 to 80 wt %, specifically 0.01 to 40 wt %, compared to the total weight of the composition, the pharmaceutical composition is not limited thereto.

A pharmaceutical composition according to the present invention may further include a pharmaceutically acceptable carrier, an excipient, or a diluent which are usually used in the preparation of the pharmaceutical composition, and the carrier may include a non-naturally occurring carrier.

The pharmaceutical composition may be formulated and used in the form of oral formulations such as a powder, a granule, a tablet, a capsule, a suspension, an emulsion, a syrup, an aerosol, etc., external preparations, suppositories, and sterilized injection solutions depending on the respective usual method.

The "pharmaceutically acceptable" means exhibiting non-toxic properties in cells or humans exposed to the composition.

Specifically, types of the carrier are not particularly limited, and anything may be used if it is a carrier which is commonly used and pharmacologically acceptable in the relevant technical field. Nonlimiting examples of the carrier may include a saline solution, sterile water, Ringer solution, a buffered saline solution, an albumin injection solution, a dextrose solution, a maltodextrin solution, glycerol, ethanol, etc. These nonlimiting examples of the carrier may be used alone or in the form of mixtures of two or more thereof. Further, if necessary, the carrier may be used in a state that other common additives such as an antioxidant, a buffer solution and/or a bacteriostatic agent are added to the carrier, and the carrier may be used in the form of the formulations by additionally adding a diluent, a dispersant, a surfactant, a bonding agent, a lubricant, etc. to the carrier, thereby forming the mixtures into formulations such as injectable formulations including an aqueous solution, a suspension, an emulsion, etc., pills, capsules, granules, tablets, or the like.

An administration method of a pharmaceutical composition for the prevention or treatment of cancer according to the present invention is not particularly limited, may follow methods usually used in the relevant technical field. Nonlimiting examples of the administration method may include a method of oral administration of the composition, and a method of parenteral administration of the composition. Further, a composition for the prevention, alleviation or treatment of cancer according to the present invention may be prepared in a variety of formulations depending on the intended administration method.

The administration amount of a pharmaceutical composition for the prevention or treatment of cancer according to the present invention varies depending on the patient's gender, age and weight, administration route, treatment adaptation, or characteristics of any related treatment, and is in the range of 0.001 to 1,000 mg/kg (weight) per 24 hours with one or more times of administration.

Nonlimiting examples of the above-mentioned anti-cancer drug have the same meaning as previously defined ones.

The anti-cancer drug may be supported on nanoparticles. Although a pharmaceutical composition including nanoparticles according to the present invention itself has anticancer effects, the pharmaceutical composition may express excellent anticancer effects by delivering the anti-cancer drug better to tumor lesions when administering the anti-cancer drug to the body in a state that the anti-cancer drug is supported on the nanoparticles compared to when administering each of the substances.

The present invention further provides an anti-cancer therapy adjuvant including the nanoparticles according to the present invention. An anti-cancer therapy adjuvant according to the present invention may exhibit excellent effects on cancer treatment by enhancing the anti-cancer effects of the nonlimiting examples of the anti-cancer drug.

The above-mentioned anti-cancer therapy adjuvant means a formulation that can improve, advance or increase anti-cancer effects by combining the anti-cancer therapy adjuvant with radiotherapy, chemical therapy, surgical treatment, or the like. Therefore, an anti-cancer therapy adjuvant according to the present invention may be used to treat cancer by treating the anti-cancer therapy adjuvant in patients simultaneously or sequentially with radiotherapy, chemical therapy, or surgical treatment.

The present invention provides a use of the composition including the nanoparticles in the manufacture of drugs for the treatment of cancer.

The present invention further provides a method of treating cancer, including the step of administering the nanoparticles to a subject that needs them in a therapeutic effective amount. A method of treating cancer according to the present invention may include the step of applying light to the affected area. That is, after administering the nanoparticles to a target that needs them in a therapeutic effective amount, the method may have anticancer effects by irradiating light in a therapeutic effective amount.

The target refers to an animal, and may be typically a mammal that can exhibit an advantageous effect with treatment using an active component of the present invention. A preferred example of such a target may include primates such as humans. Further, targets like these may include all subjects who have symptoms of cancer or are at risk of having symptoms such as these.

Another aspect of the present invention for achieving the foregoing object is to provide a method of preparing nanoparticles, the method including the steps of: 1) mixing a mussel adhesive protein with $MX_3$; and 2) electrospraying a mixture of the step 1) at a rate of 0.5 to 1.5 ml/h and a voltage of 5 to 15 kV.

The mussel adhesive protein and $MX_3$ have the same meaning as previously defined. Particularly, the above-mentioned $MX_3$ enables the DOPA-metal complex to have properties as nanoparticles by forming a DOPA-metal complex with the mussel adhesive protein.

The foregoing method of preparing nanoparticles may prepare desired sized nanoparticles through the electrospraying step. The mixture is prepared into nanoparticles by electrospraying the mixture of the step 1) at a rate of 0.5 to 1.5 ml/h and a voltage of 5 to 15 kV. A desirable example of the electrospraying rate is 1 ml/h, and a preferred example of the electrospraying voltage is 6 to 14 kV.

In the step 1). A may be additionally mixed together with the mussel adhesive protein and $MX_3$, and the above-mentioned A may be any one or more selected from the group consisting of S-nitrosoglutathione, N,N'-di-sec-butyl-N,N'-dinitroso-1,4-phenylenediamine, Roussin's black salt, and S-nitrosothiol (SNO).

In the step 1), an anti-cancer drug is mixed together with the mussel adhesive protein, $MX_3$, and A, and the anti-cancer drug may be any one or more selected from the group consisting of doxorubicin, paclitaxel, azithromycin, erythromycin, vinblastine, bleomycin, dactinomycin, daunorubicin, idarubicin, mitoxantrone, plicamycin, and mitomycin.

Another aspect of the present invention for achieving the foregoing object is to provide nanoparticles prepared by the preparation method.

The above-mentioned mussel adhesive protein-based photothermal-responsive nanoparticles according to the present invention minimizes the risk of toxicity by having excellent biocompatibility and biodegradability as a protein-based photothermal agent, enables an effective photothermal therapy by having less risk of separation from an administered region through adhesive properties, and may be applied to trimodality therapy through controlled release and anti-cancer effects of a loaded drug by reacting with light and heat, thereby generating a gas.

Advantageous Effects

Effective photothermal effects may be obtained by preparing mussel adhesive protein-based photothermal agent and photothermal-responsive nanoparticles according to the present invention through metal-catechol bonding, and the mussel adhesive protein-based photothermal agent and photothermal-responsive nanoparticles may induce annihilation of cancer cells by reacting with light and heat, thereby forming a nitric oxide gas, and may be applied as a trimodality therapy system by inducing release of a photothermal-responsive drug.

MODES OF THE INVENTION

Hereinafter, the present invention will be described in detail by Examples. However, Examples below are only for the purpose of presenting the present invention, and the present invention is not limited to the Examples below.

Example 1. Preparation of Mussel Adhesive Protein-Based Nanoparticles 1-1. Preparation of Mussel Adhesive Protein Fp-1

First, a variant of a mussel adhesive protein fp-1 (*Mytilus* mussel foot protein type 1) to which decapeptides (AKPSYPPTYK (SEQ ID NO: 2)) had been repeatedly connected 12 times was prepared according to a publicly known procedure (See: Proc. Natl. Acad. Sci. USA 2010, 107, 12850-3). The mussel adhesive protein fp-1 prepared as described above was allowed to be successfully expressed in *E. coli*, and then, it was produced through the purification and separation process using acetic acid.

1-2. DOPA Modification Reaction

In order to obtain a mussel adhesive protein into which DOPA was introduced, a modification reaction using a tyrosinase enzyme (mushroom tyrosinase) was performed in vitro to convert tyrosine residues into DOPA. Specifically, 150 mg of a mussel adhesive protein and 5 mg of tyrosinase were added to 100 mL of a buffer solution consisting of 100 mM sodium phosphate, 20 mM boric acid and 25 mM ascorbic acid, and having a pH value of 6.8, and reacted for 1 hour. Thereafter, dialysis was performed using 5 L of a 5% acetic acid solution, followed by lyophilization to prepare a mussel adhesive protein into which DOPA was introduced.

1-3. Preparation of Nanoparticles Using Mussel Adhesive Protein

Figure 1:
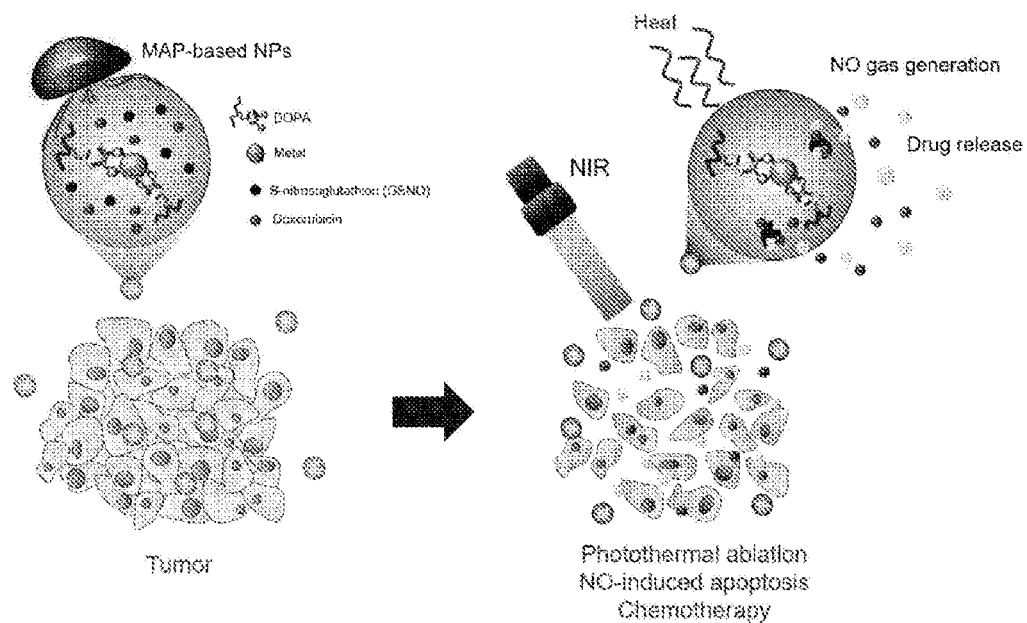
FIG. 1 is a schematic diagram showing that photothermal effects are caused through near-infrared rays to induce annihilation of the cancer cells when applying a photothermal agent based on a mussel adhesive protein and nanoparticles containing a photothermal-responsive gas donor and a drug according to the present invention to cancer cells, and complex anti-cancer effects are obtained by inducing the generation of a nitric oxide gas, thereby releasing the drug.
Figure 2:
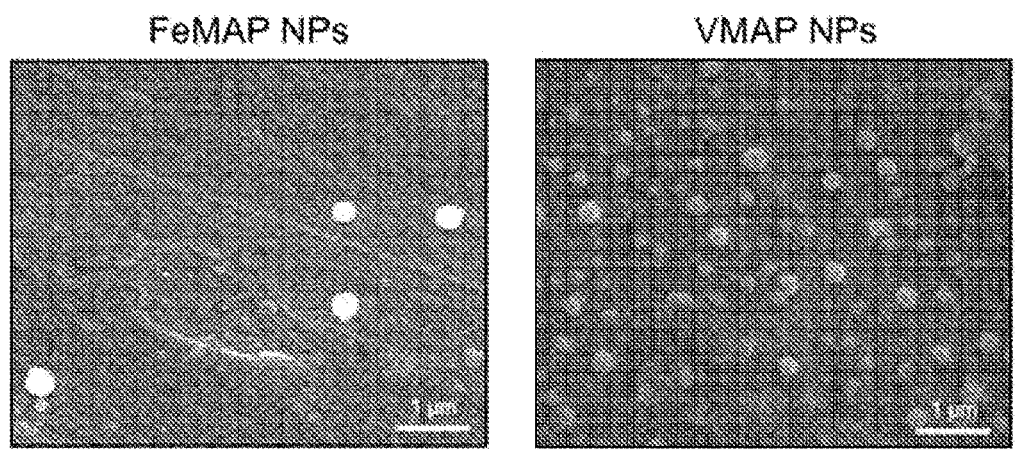
FIG. 2 is scanning electron microscope (SEM) images of nanoparticles (FeMAP NPs, VMAP NPs) prepared by forming a metal-catechol complex through iron (Fe) ions and vanadium (V) ions, i.e., metal ions.

Nanoparticles were prepared through electrospraying technology using the DOPA-introduced mussel adhesive protein fp-1 which had been obtained through Example 1-2. Specifically, the nanoparticles were dissolved in a solvent containing 2 wt % of MAP distilled water and ethanol at a ratio of 30:70, and then an $FeCl_3$ solution or a $VCl_3$ solution was added, followed by mixing so that the ratio of DOPA-Fe or DOPA-V became a molar ratio of 3:1. Thereafter, electrospraying was performed in a high voltage environment of 6 to 14 kV while injecting the solution at a rate of 1 mL/h using a syringe pump. The produced nanoparticles were collected in a phosphate-buffered saline (PBS, pH 7.4). The collected nanoparticles were analyzed using a scanning electron microscope (SEM), and the analysis results are shown in FIG. 2.

The specific preparation of the mussel adhesive protein is the same as that shown in Patent Application No. 10-2015-0035270, and the patent document is included in the present invention by reference as a whole.

Figure 3:
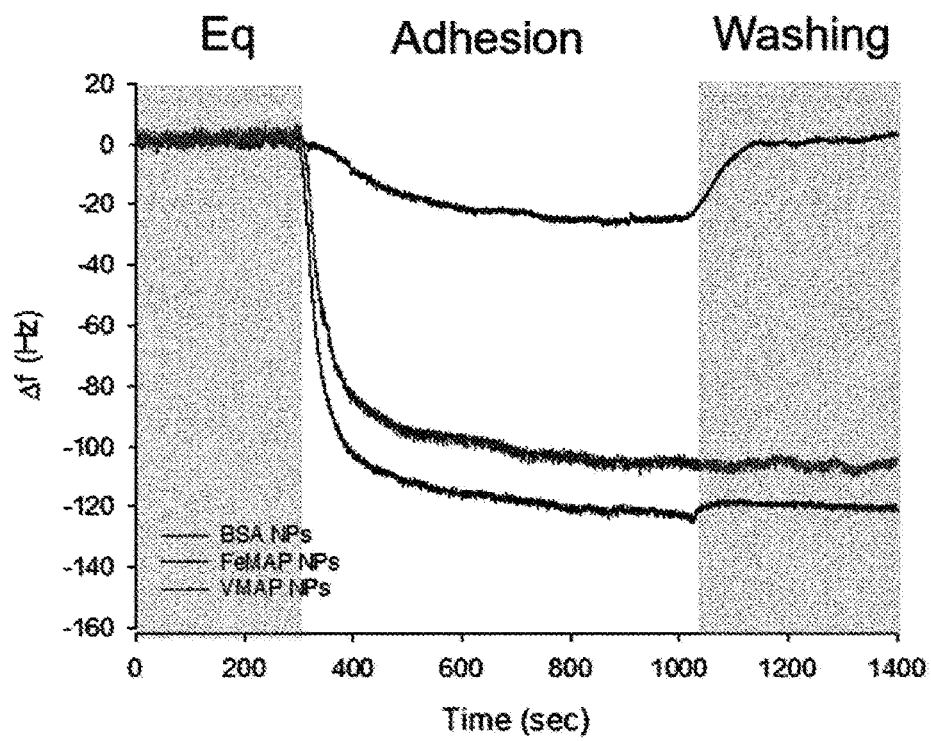
FIG. 3, as results of measuring adhesion values of the respective nanoparticles according to Example 1 using QCM, shows results of comparing the measured adhesion values of the nanoparticles by using bovine serum albumin (BSA) nanoparticles as a control group.

1-4. Analysis of Adhesive Properties of Nanoparticles Using Mussel Adhesive Protein Adhesive properties of nanoparticles (FeMAP NPs) containing the prepared DOPA-Fe complex and nanoparticles (VMAP NPs) containing a DOPA-V complex were analyzed using a quartz crystal monitor sensor (QCM). After stabilizing the mussel adhesive protein for 10 minutes by administering distilled water to a mussel adhesive protein at a rate of 0.2 ml/min using a flow meter, a change in frequency was measured while administering 1 mg/ml of a nanoparticle solution to the mussel adhesive protein at the same rate for 10 minutes. Thereafter, the frequency change was measured while administering distilled water for washing to the mussel adhesive protein. In this case, bovine serum albumin (BSA)-based nanoparticles (BSA NPs) were used as a control group. As a result, the frequency changes of FeMAP NPs and VMAP NPs were about −115.82 Hz and −108.00 Hz respectively, showing a greater frequency change than −23.24 Hz, which was the frequency change of BSA NPs (FIG. 3). In addition, the frequency of BSA NPs was increased to −4.73 Hz during the washing process, whereas frequencies of FeMAP NPs and VMAP NPs were −114.44 Hz and −106.45 Hz respectively, indicating that there was no change in frequency, thereby confirming that the FeMAP NPs and VMAP NPs were continuously adhered to the surface.

Example 2. Analysis of Photothermal Effects of Mussel Adhesive Protein-Based Nanoparticles 2-1. Analysis of Absorbance of Nanoparticles Absorbances in the near-infrared region of the FeMAP NPs and VMAP NPs prepared in Example 1-3 were analyzed through a UV-vis spectrometer, and the analysis results are shown in FIG. 4.

Figure 4:
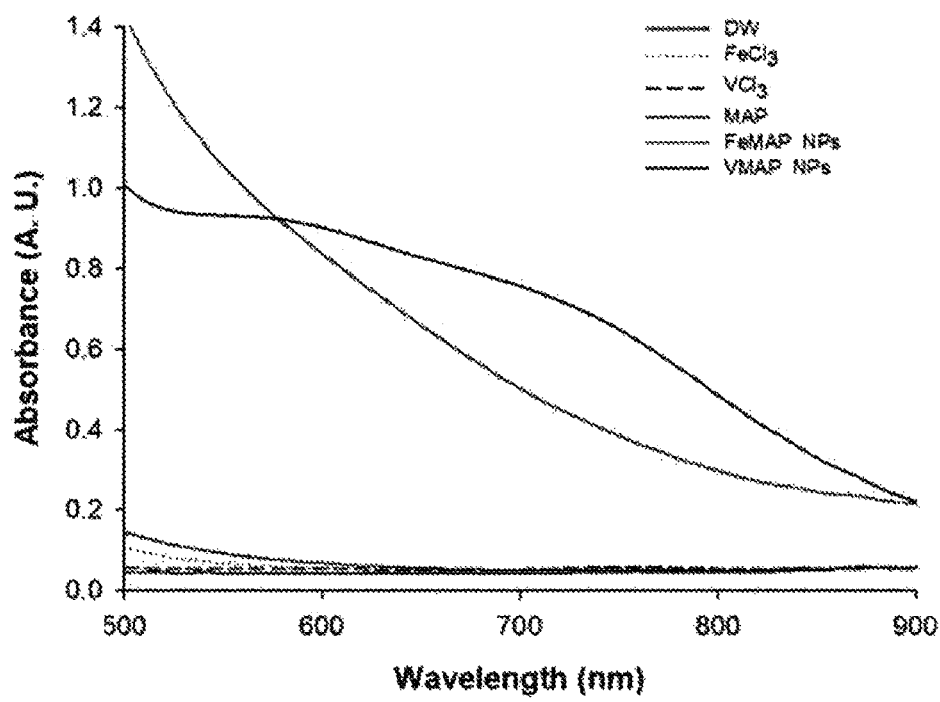
FIG. 4 is a graph showing comparison results obtained by comparing UV absorption spectrums of the respective nanoparticles according to Example 2 using deionized water (DW), $FeCl_3$, $VCl_3$, and a mussel adhesive protein (MAP) as a control group.

As shown in FIG. 4, when absorption spectrums were measured at 500 nm to 900 nm, a protein solution containing no DW, $FeCl_3$, $VCl_3$, and DOPA-metal complex showed almost no absorbance, whereas FeMAP NPs and VMAP NPs containing the DOPA-metal complex showed an increase in absorbance, and in particular, it was confirmed that the absorbances at 808 nm were 0.2838 and 0.4523 respectively.

2-2. Analysis of Photothermal Effects of Nanoparticles

After 1 mL of FeMAP NPs and VMAP NPs prepared in Example 1-3 were each put into a cuvette, near-infrared rays were applied in a determined time period using an 808 nm laser having a power of 2 $W/cm^2$. The temperature of the solution was measured using a thermometer at each time period and shown in FIG. 5

Figure 5:
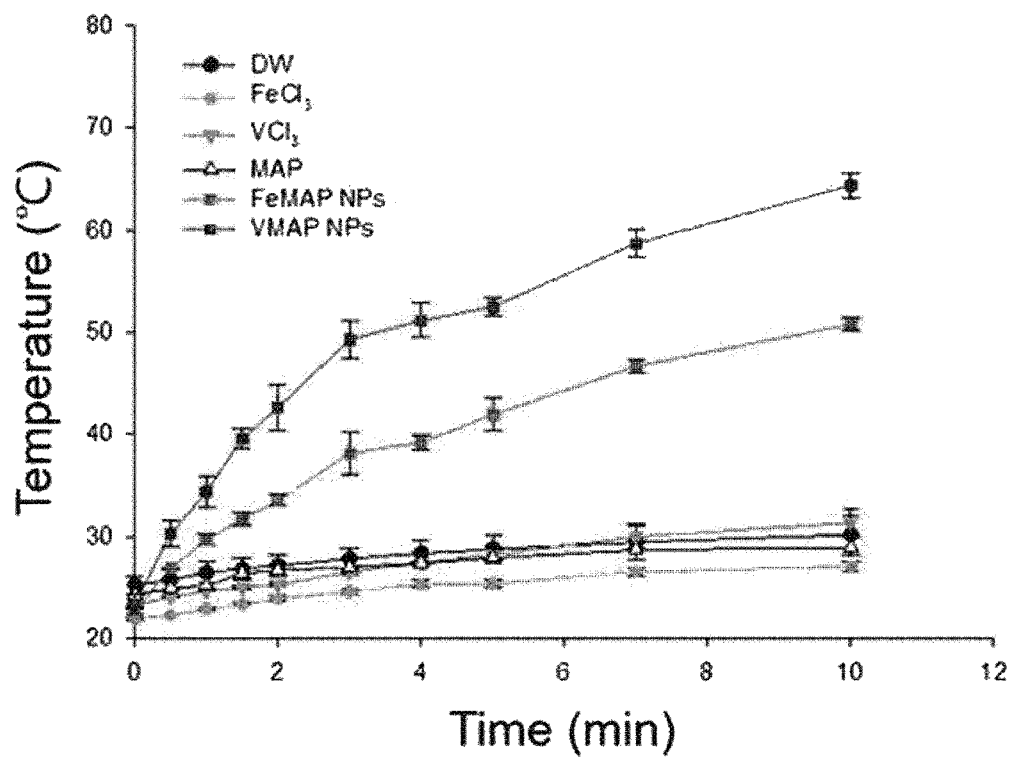
FIG. 5 is a graph measuring temperature values generated when applying near-infrared rays to the respective nanoparticles according to Example 2.

As shown in FIG. 5, it was confirmed that each of the nanoparticles generated heat when the near-infrared rays were applied and the temperature increased to 50° C. or higher within 10 minutes. Compared to FeMAP NPs, VMAP NPs exhibited also higher photothermal effects because absorbance in the near-infrared region was higher, and it was confirmed that the temperature increased to 50° C. or higher within 5 minutes. Accordingly, it was confirmed that the nanoparticles containing the DOPA-metal complex may be used as a photothermal agent in the near-infrared region.

Figure 6:
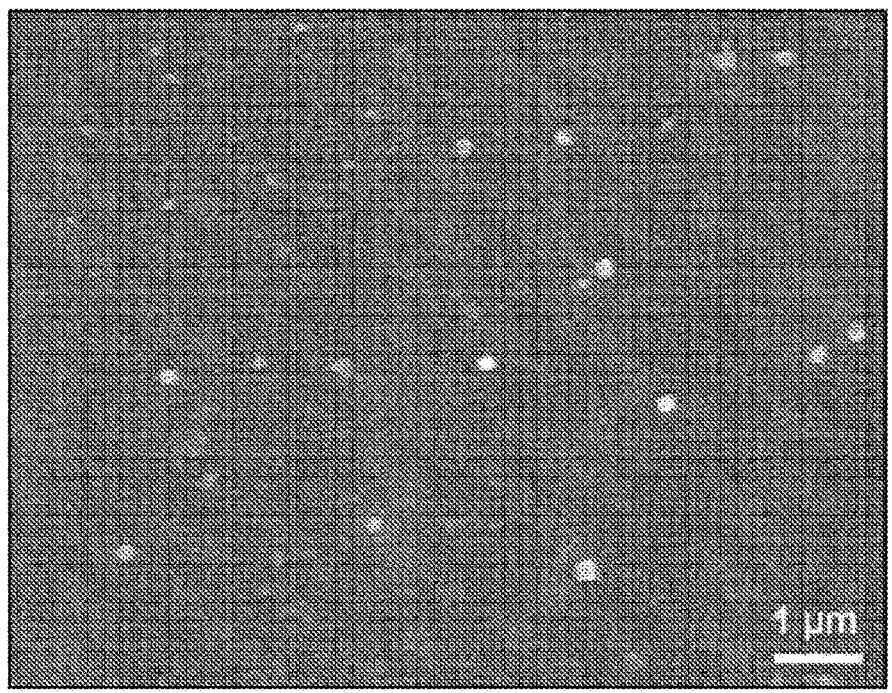
FIG. 6 is an SEM image of nanoparticles (VMAP@GSNO NPs) containing S-nitrosoglutathione (GSNO) that is a nitric oxide gas donor according to Example 3.

Example 3. Analysis of Gas Formation of Mussel Adhesive Protein-Based Nanoparticles 3-1. Preparation of Photothermal-Responsive Nanoparticles Loaded with GSNO Photothermal-responsive nanoparticles (VMAP@GSNO NPs) loaded with GSNO were prepared in the same manner as in Example 1-3. Specifically, the nanoparticles were dissolved in a solvent containing 2 wt % of MAP distilled water and ethanol at a ratio of 30:70, and then a $VCl_3$ solution was added, followed by mixing so that the ratio of DOPA-V became a molar ratio of 3:1. Thereafter, 100 mM GSNO solution was added to the solution to be 40 μM, and then electrospraying was performed in a high voltage environment of 6 to 14 kV while injecting the GSNO solution-added solution at a rate of 1 mL/h using a syringe pump. The produced nanoparticles were put in a dialysis membrane of MWCO (molecular weight cut off) 3500, and then dialysis was performed using PBS (pH 7.4) to remove unloaded GSNO. Thereafter, the nanoparticles were analyzed using a scanning electron microscope (SEM), and the analysis results are shown in FIG. 6.

Figure 7:
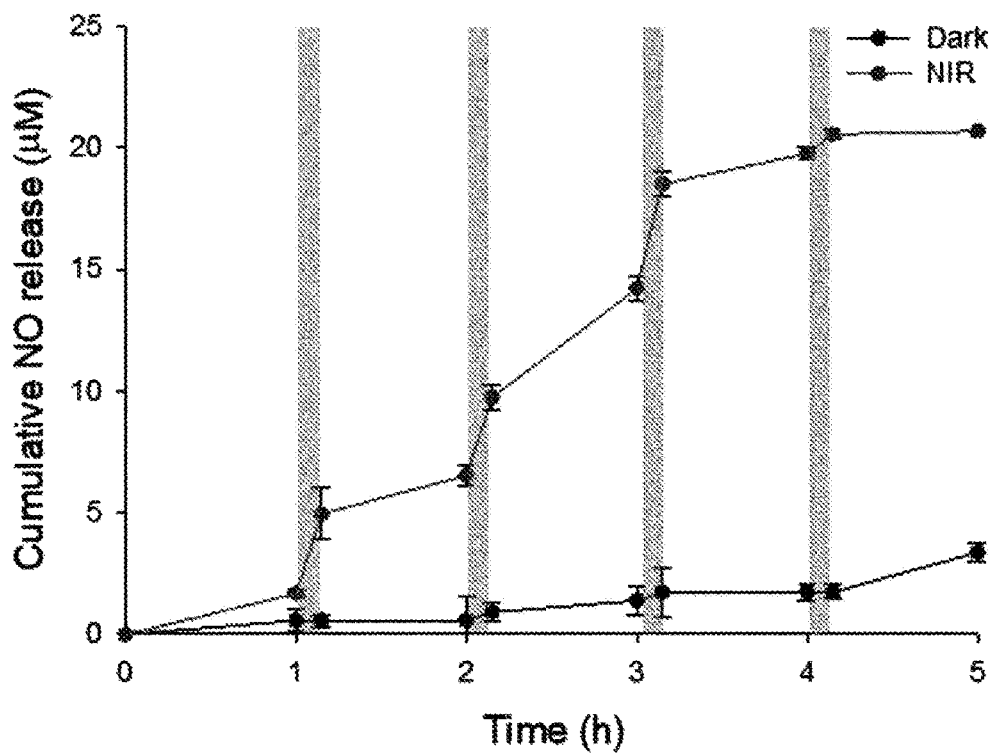
FIG. 7 is a graph measuring the generation of a nitric oxide gas of VMAP@GSNO nanoparticles according to Example 3. GSNO was used as a control group.

3-2. Analysis of Photothermal-Responsive Nitric Oxide Gas Formation of Nanoparticles Loaded with GSNO The photothermal-responsive nitric oxide gas formation of VMAP@GSNO NPs prepared in Example 3-1 was confirmed using a Griess reagent. 1 mL of an aqueous solution containing 9 mg/mL of VMAP@GSNO NPs was tubed into an MWCO 3.5 kDa membrane and cultured in 1 mL of PBS (pH 7.4). While applying a near-infrared laser at 1 hour intervals for 10 minutes, each solution was sampled and replaced with a new PBS solution. The formed nitric oxide gas was measured by mixing the sampled solution and the Griess reagent at a ratio of 1:1, and measuring the absorbance at 540 nm after 15 minutes. As a control group, a VMAP@GSNO NPs solution was sampled without applying a near-infrared laser. As a result, when the laser was not applied, the release of nitric oxide hardly occurred, but it was found that the release of nitric oxide occurred in the solution to which the laser was applied (FIG. 7).

Figure 8:
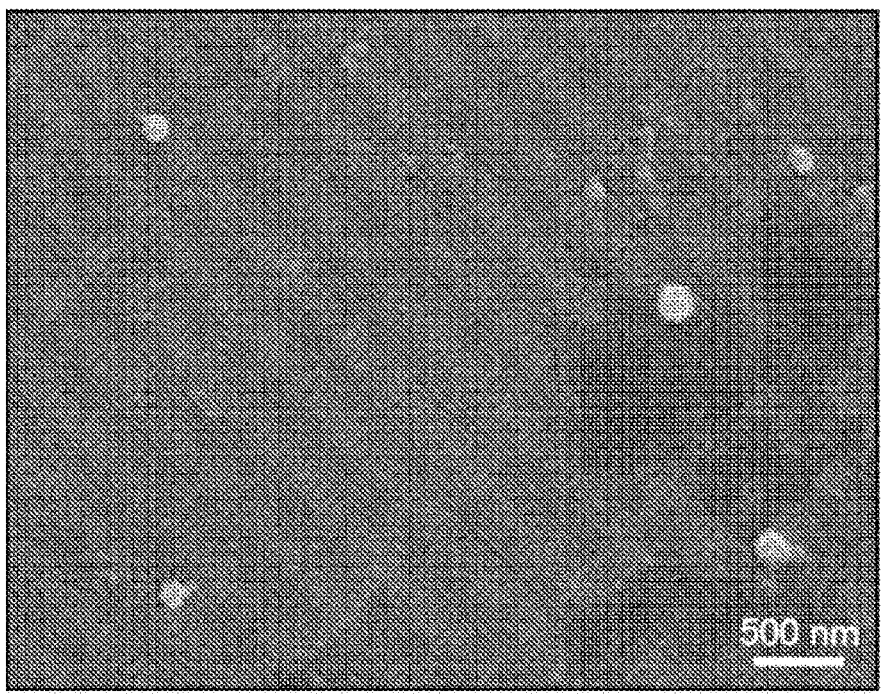
FIG. 8 is an SEM image of nanoparticles (VMAP@GSNO/DOX nanoparticles) containing GSNO and DOX according to Example 4.

Example 4. Analysis of Drug Release Patterns of Mussel Adhesive Protein-Based Nanoparticles 4-1. Preparation of Photothermal-Responsive Nanoparticles Loaded with GSNO and Anti-Cancer Drugs at the Same Time Photothermal-responsive nanoparticles (VMAP@GSNO/DOX NPs) loaded with GSNO and the anti-cancer drug doxorubicin (DOX) at the same time were prepared in the same manner as in Example 1-3. Specifically, the VMAP@GSNO/DOX NPs were dissolved in a solvent containing 2 wt % of MAP distilled water and ethanol at a ratio of 30:70, and then a $VCl_3$ solution was added, followed by mixing so that the ratio of DOPA-V became a molar ratio of 3:1. Thereafter, the GSNO solution and the DOX solution were added to the solution, and then electrospraying was performed in a high voltage environment of 6 to 14 kV while injecting at a rate of 1 mL/h using a syringe pump. The produced nanoparticles were put in a dialysis membrane of MWCO (molecular weight cut off) 3500, and then dialyzed using PBS (pH 7.4) to remove unloaded GSNO and DOX. Thereafter, the nanoparticles were analyzed using a scanning electron microscope (SEM), and the analysis results are shown in FIG. 8.

Figure 9:
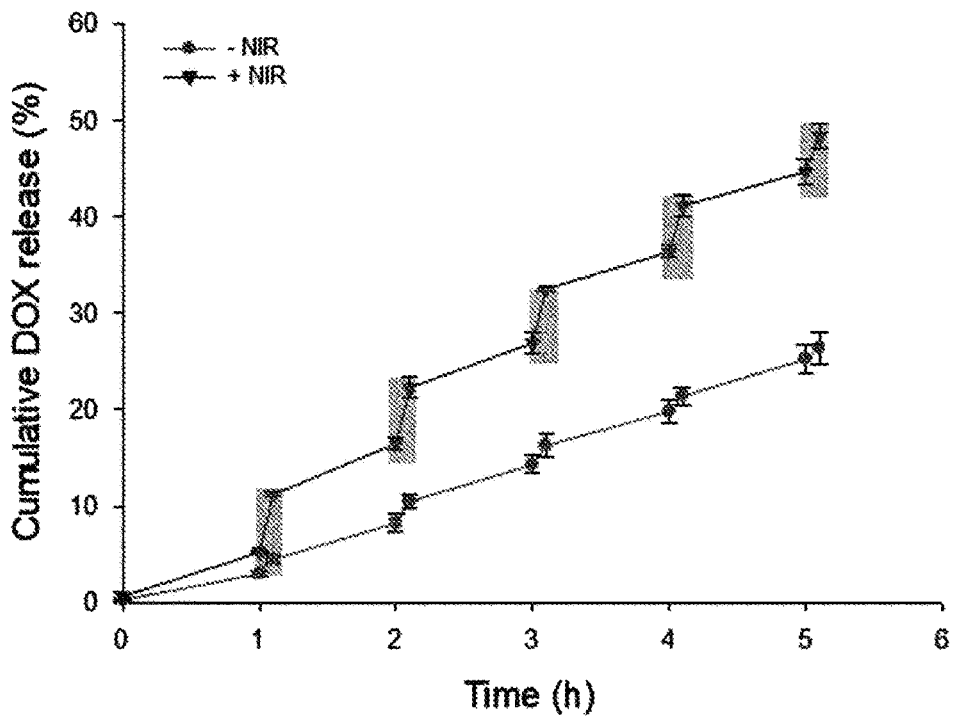
FIG. 9 shows a graph measuring the drug release of VMAP@GSNO/DOX nanoparticles according to Example 4.

4-2. Analysis of Photothermal-Responsive Drug Release Patterns of Nanoparticles Loaded with GSNO The photothermal-responsive drug release patterns of VMAP@GSNO/DOX NPs prepared in Example 4-1 were measured in vitro. 1 mL of an aqueous solution containing 9 mg/mL of VMAP@GSNO/DOX NPs was tubed into an MWCO 3.5 kDa membrane and cultured in 1 mL of PBS (pH 7.4). While applying a near-infrared laser at 1 hour intervals for 10 minutes, each solution was sampled and replaced with a new PBS solution. The amount of released DOX was measured through a fluorescence spectrum at an excitation wavelength of 485 nm and an emission wavelength of 580/10 nm. As a control group, a VMAP@GSNO/DOX NPs solution was sampled without applying a near-infrared laser. As a result, when the laser was not applied, the release of DOX hardly occurred, but it was found that the release of DOX occurred in the solution to which the laser was applied (FIG. 9).

Figure 10:
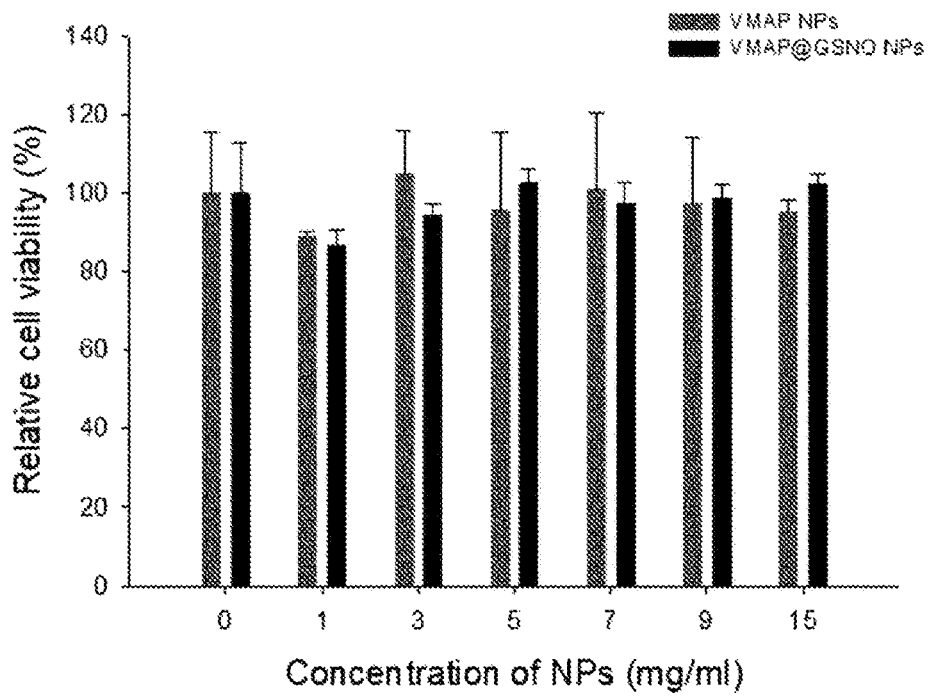
FIG. 10 shows a graph of MCF7 cell viability when near-infrared rays are not applied in Example 5.

Example 5. Confirmation of Cytotoxicity and Anti-Cancer Effects of Photothermal-Responsive Nanoparticles 5-1. Confirmation of Cytotoxicity of Photothermal-Responsive Nanoparticles The cytotoxicity of the VMAP NPs and VMAP@GSNO NPs prepared in Examples 1-3 and 3-1 to human-derived breast cancer cells MCF7 (ATCC HTB-22) was confirmed. First, MCF7 cells were seeded in an amount of $1 \times 10^4$ cells per well using a 48-well culture plate, and cultured at 37° C. in a humid atmosphere of 5% $CO_2$ and 95% air for 1 day. Then, 9 mg/ml of each of the NPs was treated in a medium and cultured for 24 hours, and then cell viability was measured. Cell viability was determined by treating the CCK-8 reagent and performing a culturing process for 3 hours, and then measuring the absorbance at 450 nm from an aliquot of each medium (FIG. 10). Cells which had not been treated with nanoparticles were used as a control group.

As shown in FIG. 10, cell viabilities of VMAP NPs and VMAP@GSNO NPs were about 90 to 105% and 85 to 102% respectively, and it was confirmed that no cytotoxicity appeared compared to the control group.

5-2. Confirmation of Anti-Cancer Effects of Photothermal-Responsive Nanoparticles The cell viability of each cell according to the photothermal time of the photothermal-responsive nanoparticles was confirmed. Specifically, MCF7 cells were seeded in an amount of $1 \times 10^4$ cells per well in a 48-well culture plate, and cultured at 37° C. in a humid atmosphere of 5% $CO_2$ and 95% air for 1 day. Thereafter, 9 mg/ml of VMAP NPs, VMAP@GSNO NPs, and VMAP@GSNO/DOX NPs were treated in the medium and cultured for 30 minutes, followed by application of a near-infrared laser at 808 nm for 2 minutes, 5 minutes, and 10 minutes. Thereafter, a new medium was added and cultured for 24 hours, and then cell viability was measured using a CCK-8 reagent. Cells to which the laser was applied each hour without treatment with nanoparticles were used as a control group, and the results are shown in FIG. 11.

Figure 11:
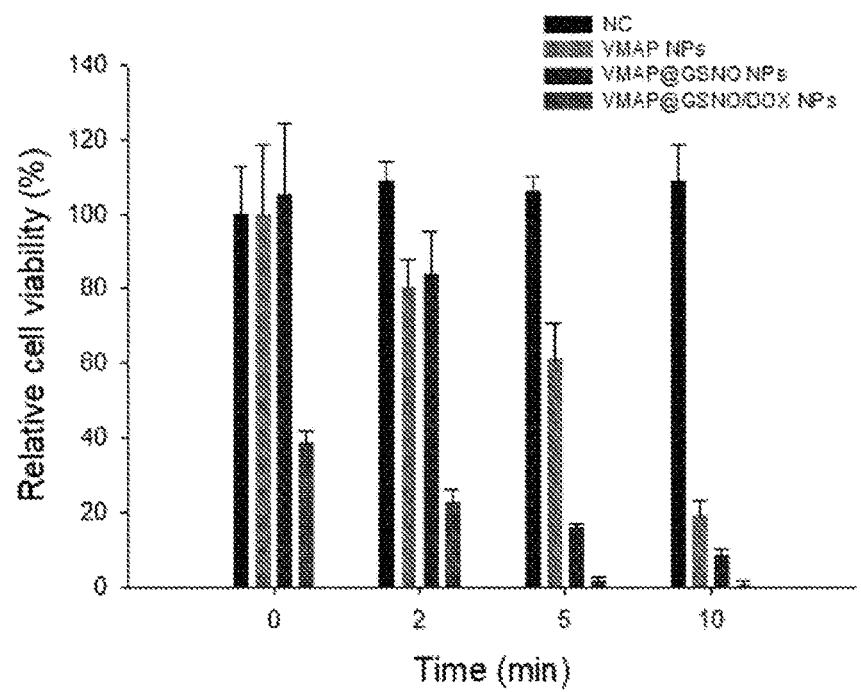
FIG. 11 shows a graph of MCF7 cell viability according to time values at which near-infrared rays are applied in Example 5.

As shown in FIG. 11, as the time to apply the laser increases, the cell viability decreases, and when applied for 10 minutes, the anti-cancer effect according to the photothermal effect was confirmed by confirming that cell viabilities of VMAP NPs and VMAP@GSNO NPs were about 20% and 8.5% respectively. When the laser was applied for 10 minutes, the cell viability of VMAP@GSNO/DOX NPs was about 0.5%, and it was confirmed that trimodality therapy showed better anti-cancer effects through photothermal effect, nitric oxide gas, and anti-cancer drug.

The invention claimed is:

1. Photothermal-responsive adhesive nanoparticles comprising
   a mussel adhesive protein consisting of the amino acid sequence of SEQ ID NO: 9,
   S-nitrosoglutathione as a photothermal-responsive gas donor, and
   VCl$_3$ as a transition metal halide.

2. The photothermal-responsive adhesive nanoparticles of claim 1, wherein the mussel adhesive protein is characterized in that 10 to 100% of the total tyrosine residues are modified into DOPA.

3. The photothermal-responsive adhesive nanoparticles of claim 1, further comprising doxorubicin as an anti-cancer drug.

4. The photothermal-responsive adhesive nanoparticles of claim 1, wherein the gas is nitric oxide.

* * * * *

SEQUENCE LISTING

<160> NUMBER OF SEQ ID NOS: 16

<210> SEQ ID NO 1
<211> LENGTH: 800
<212> TYPE: PRT
<213> ORGANISM: Artificial Sequence
<220> FEATURE:
<223> OTHER INFORMATION: fp-1

<400> SEQUENCE: 1

-continued

```
Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
            20                  25                  30

Pro Ser Tyr Pro Pro Thr Tyr Lys Ala Lys Pro Ser Tyr Pro Pro Thr
        35                  40                  45

Tyr Lys Ala Lys Pro Ser Tyr Pro Pro Thr Tyr Lys Ala Lys Pro Ser
    50                  55                  60

Tyr Pro Pro Thr Tyr Lys Ala Lys Pro Ser Tyr Pro Pro Thr Tyr Lys
65                  70                  75                  80

Ala Lys Pro Ser Tyr Pro Pro Thr Tyr Lys Ala Lys Pro Ser Tyr Pro
                85                  90                  95

Pro Thr Tyr Lys Ala Lys Pro Ser Tyr Pro Pro Thr Tyr Lys Ala Lys
            100                 105                 110

Pro Ser Tyr Pro Pro Thr Tyr Lys Ala Lys Pro Ser Tyr Pro Pro Thr
        115                 120                 125

Tyr Lys Ala Lys Pro Ser Tyr Pro Pro Thr Tyr Lys Ala Lys Pro Ser
    130                 135                 140

Tyr Pro Pro Thr Tyr Lys Ala Lys Pro Ser Tyr Pro Pro Thr Tyr Lys
145                 150                 155                 160

Ala Lys Pro Ser Tyr Pro Pro Thr Tyr Lys Ala Lys Pro Ser Tyr Pro
                165                 170                 175

Pro Thr Tyr Lys Ala Lys Pro Ser Tyr Pro Pro Thr Tyr Lys Ala Lys
            180                 185                 190

Pro Ser Tyr Pro Pro Thr Tyr Lys Ala Lys Pro Ser Tyr Pro Pro Thr
        195                 200                 205

Tyr Lys Ala Lys Pro Ser Tyr Pro Pro Thr Tyr Lys Ala Lys Pro Ser
    210                 215                 220

Tyr Pro Pro Thr Tyr Lys Ala Lys Pro Ser Tyr Pro Pro Thr Tyr Lys
225                 230                 235                 240

Ala Lys Pro Ser Tyr Pro Pro Thr Tyr Lys Ala Lys Pro Ser Tyr Pro
                245                 250                 255

Pro Thr Tyr Lys Ala Lys Pro Ser Tyr Pro Pro Thr Tyr Lys Ala Lys
            260                 265                 270

Pro Ser Tyr Pro Pro Thr Tyr Lys Ala Lys Pro Ser Tyr Pro Pro Thr
        275                 280                 285

Tyr Lys Ala Lys Pro Ser Tyr Pro Pro Thr Tyr Lys Ala Lys Pro Ser
    290                 295                 300

Tyr Pro Pro Thr Tyr Lys Ala Lys Pro Ser Tyr Pro Pro Thr Tyr Lys
305                 310                 315                 320

Ala Lys Pro Ser Tyr Pro Pro Thr Tyr Lys Ala Lys Pro Ser Tyr Pro
                325                 330                 335

Pro Thr Tyr Lys Ala Lys Pro Ser Tyr Pro Pro Thr Tyr Lys Ala Lys
            340                 345                 350

Pro Ser Tyr Pro Pro Thr Tyr Lys Ala Lys Pro Ser Tyr Pro Pro Thr
        355                 360                 365

Tyr Lys Ala Lys Pro Ser Tyr Pro Pro Thr Tyr Lys Ala Lys Pro Ser
    370                 375                 380

Tyr Pro Pro Thr Tyr Lys Ala Lys Pro Ser Tyr Pro Pro Thr Tyr Lys
385                 390                 395                 400

Ala Lys Pro Ser Tyr Pro Pro Thr Tyr Lys Ala Lys Pro Ser Tyr Pro
                405                 410                 415
```

Pro Thr Tyr Lys Ala Lys Pro Ser Tyr Pro Pro Thr Tyr Lys Ala Lys
                420                 425                 430

Pro Ser Tyr Pro Pro Thr Tyr Lys Ala Lys Pro Ser Tyr Pro Pro Thr
        435                 440                 445

Tyr Lys Ala Lys Pro Ser Tyr Pro Pro Thr Tyr Lys Ala Lys Pro Ser
450                 455                 460

Tyr Pro Pro Thr Tyr Lys Ala Lys Pro Ser Tyr Pro Pro Thr Tyr Lys
465                 470                 475                 480

Ala Lys Pro Ser Tyr Pro Pro Thr Tyr Lys Ala Lys Pro Ser Tyr Pro
                485                 490                 495

Pro Thr Tyr Lys Ala Lys Pro Ser Tyr Pro Pro Thr Tyr Lys Ala Lys
                500                 505                 510

Pro Ser Tyr Pro Pro Thr Tyr Lys Ala Lys Pro Ser Tyr Pro Pro Thr
        515                 520                 525

Tyr Lys Ala Lys Pro Ser Tyr Pro Pro Thr Tyr Lys Ala Lys Pro Ser
530                 535                 540

Tyr Pro Pro Thr Tyr Lys Ala Lys Pro Ser Tyr Pro Pro Thr Tyr Lys
545                 550                 555                 560

Ala Lys Pro Ser Tyr Pro Pro Thr Tyr Lys Ala Lys Pro Ser Tyr Pro
                565                 570                 575

Pro Thr Tyr Lys Ala Lys Pro Ser Tyr Pro Pro Thr Tyr Lys Ala Lys
                580                 585                 590

Pro Ser Tyr Pro Pro Thr Tyr Lys Ala Lys Pro Ser Tyr Pro Pro Thr
        595                 600                 605

Tyr Lys Ala Lys Pro Ser Tyr Pro Pro Thr Tyr Lys Ala Lys Pro Ser
610                 615                 620

Tyr Pro Pro Thr Tyr Lys Ala Lys Pro Ser Tyr Pro Pro Thr Tyr Lys
625                 630                 635                 640

Ala Lys Pro Ser Tyr Pro Pro Thr Tyr Lys Ala Lys Pro Ser Tyr Pro
                645                 650                 655

Pro Thr Tyr Lys Ala Lys Pro Ser Tyr Pro Pro Thr Tyr Lys Ala Lys
                660                 665                 670

Pro Ser Tyr Pro Pro Thr Tyr Lys Ala Lys Pro Ser Tyr Pro Pro Thr
        675                 680                 685

Tyr Lys Ala Lys Pro Ser Tyr Pro Pro Thr Tyr Lys Ala Lys Pro Ser
690                 695                 700

Tyr Pro Pro Thr Tyr Lys Ala Lys Pro Ser Tyr Pro Pro Thr Tyr Lys
705                 710                 715                 720

Ala Lys Pro Ser Tyr Pro Pro Thr Tyr Lys Ala Lys Pro Ser Tyr Pro
                725                 730                 735

Pro Thr Tyr Lys Ala Lys Pro Ser Tyr Pro Pro Thr Tyr Lys Ala Lys
                740                 745                 750

Pro Ser Tyr Pro Pro Thr Tyr Lys Ala Lys Pro Ser Tyr Pro Pro Thr
        755                 760                 765

Tyr Lys Ala Lys Pro Ser Tyr Pro Pro Thr Tyr Lys Ala Lys Pro Ser
770                 775                 780

Tyr Pro Pro Thr Tyr Lys Ala Lys Pro Ser Tyr Pro Pro Thr Tyr Lys
785                 790                 795                 800

<210> SEQ ID NO 2
<211> LENGTH: 10
<212> TYPE: PRT
<213> ORGANISM: Artificial Sequence
<220> FEATURE:
<223> OTHER INFORMATION: fp-1 variant

```
<400> SEQUENCE: 2

Ala Lys Pro Ser Tyr Pro Pro Thr Tyr Lys
1               5                   10

<210> SEQ ID NO 3
<211> LENGTH: 120
<212> TYPE: PRT
<213> ORGANISM: Artificial Sequence
<220> FEATURE:
<223> OTHER INFORMATION: fp-1 variant

<400> SEQUENCE: 3

Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
            20                  25                  30

Pro Ser Tyr Pro Pro Thr Tyr Lys Ala Lys Pro Ser Tyr Pro Pro Thr
        35                  40                  45

Tyr Lys Ala Lys Pro Ser Tyr Pro Pro Thr Tyr Lys Ala Lys Pro Ser
    50                  55                  60

Tyr Pro Pro Thr Tyr Lys Ala Lys Pro Ser Tyr Pro Pro Thr Tyr Lys
65                  70                  75                  80

Ala Lys Pro Ser Tyr Pro Pro Thr Tyr Lys Ala Lys Pro Ser Tyr Pro
                85                  90                  95

Pro Thr Tyr Lys Ala Lys Pro Ser Tyr Pro Pro Thr Tyr Lys Ala Lys
            100                 105                 110

Pro Ser Tyr Pro Pro Thr Tyr Lys
        115                 120

<210> SEQ ID NO 4
<211> LENGTH: 472
<212> TYPE: PRT
<213> ORGANISM: Artificial Sequence
<220> FEATURE:
<223> OTHER INFORMATION: fp-2

<400> SEQUENCE: 4

Leu Phe Ser Phe Phe Leu Leu Leu Thr Cys Thr Gln Leu Cys Leu Gly
1               5                   10                  15

Thr Asn Arg Pro Asp Tyr Asn Asp Asp Glu Glu Asp Tyr Lys Pro
            20                  25                  30

Pro Val Tyr Lys Pro Ser Pro Ser Lys Tyr Arg Pro Val Asn Pro Cys
        35                  40                  45

Leu Lys Lys Pro Cys Lys Tyr Asn Gly Val Cys Lys Pro Arg Gly Gly
    50                  55                  60

Ser Tyr Lys Cys Phe Cys Lys Gly Gly Tyr Gly Tyr Asn Cys Asn
65                  70                  75                  80

Leu Lys Asn Ala Cys Lys Pro Asn Gln Cys Lys Asn Lys Ser Arg Cys
                85                  90                  95

Val Pro Val Gly Lys Thr Phe Lys Cys Val Cys Arg Asn Gly Asn Phe
                100                 105                 110

Gly Arg Leu Cys Glu Lys Asn Val Cys Ser Pro Asn Pro Cys Lys Asn
            115                 120                 125

Asn Gly Lys Cys Ser Pro Leu Gly Lys Thr Tyr Lys Cys Thr Cys
        130                 135                 140

Ser Gly Gly Tyr Thr Gly Pro Arg Cys Glu Val His Ala Cys Lys Pro
145                 150                 155                 160
```

```
Asn Pro Cys Lys Asn Lys Gly Arg Cys Phe Pro Asp Gly Thr Gly
                165                 170                 175

Tyr Lys Cys Arg Cys Val Asp Gly Tyr Ser Gly Pro Thr Cys Gln Glu
            180                 185                 190

Asn Ala Cys Lys Pro Asn Pro Cys Ser Asn Gly Gly Thr Cys Ser Ala
        195                 200                 205

Asp Lys Phe Gly Asp Tyr Ser Cys Glu Cys Arg Pro Gly Tyr Phe Gly
    210                 215                 220

Pro Glu Cys Glu Arg Tyr Val Cys Ala Pro Asn Pro Cys Lys Asn Gly
225                 230                 235                 240

Gly Ile Cys Ser Ser Asp Gly Ser Gly Tyr Arg Cys Arg Cys Lys
            245                 250                 255

Gly Gly Tyr Ser Gly Pro Thr Cys Lys Val Asn Val Cys Lys Pro Thr
            260                 265                 270

Pro Cys Lys Asn Ser Gly Arg Cys Val Asn Lys Gly Ser Ser Tyr Asn
        275                 280                 285

Cys Ile Cys Lys Gly Gly Tyr Ser Gly Pro Thr Cys Gly Glu Asn Val
    290                 295                 300

Cys Lys Pro Asn Pro Cys Gln Asn Arg Gly Arg Cys Tyr Pro Asp Asn
305                 310                 315                 320

Ser Asp Asp Gly Phe Lys Cys Arg Cys Val Gly Gly Tyr Lys Gly Pro
            325                 330                 335

Thr Cys Glu Asp Lys Pro Asn Pro Cys Asn Thr Lys Pro Cys Lys Asn
            340                 345                 350

Gly Gly Lys Cys Asn Tyr Asn Gly Lys Ile Tyr Thr Cys Lys Cys Ala
        355                 360                 365

Tyr Gly Trp Arg Gly Arg His Cys Thr Asp Lys Ala Tyr Lys Pro Asn
    370                 375                 380

Pro Cys Val Val Ser Lys Pro Cys Lys Asn Arg Gly Lys Cys Ile Trp
385                 390                 395                 400

Asn Gly Lys Ala Tyr Arg Cys Lys Cys Ala Tyr Gly Tyr Gly Gly Arg
            405                 410                 415

His Cys Thr Lys Lys Ser Tyr Lys Asn Pro Cys Ala Ser Arg Pro
            420                 425                 430

Cys Lys Asn Arg Gly Lys Cys Thr Asp Lys Gly Asn Gly Tyr Val Cys
        435                 440                 445

Lys Cys Ala Arg Gly Tyr Ser Gly Arg Tyr Cys Ser Leu Lys Ser Pro
    450                 455                 460

Pro Ser Tyr Asp Asp Glu Tyr
465                 470

<210> SEQ ID NO 5
<211> LENGTH: 50
<212> TYPE: PRT
<213> ORGANISM: Artificial Sequence
<220> FEATURE:
<223> OTHER INFORMATION: fp-3

<400> SEQUENCE: 5

Pro Trp Ala Asp Tyr Tyr Gly Pro Lys Tyr Gly Pro Pro Arg Arg Tyr
1               5                   10                  15

Gly Gly Gly Asn Tyr Asn Arg Tyr Gly Arg Arg Tyr Gly Gly Tyr Lys
            20                  25                  30

Gly Trp Asn Asn Gly Trp Lys Arg Gly Arg Trp Gly Arg Lys Tyr Tyr
        35                  40                  45
```

Gly Ser
   50

<210> SEQ ID NO 6
<211> LENGTH: 750
<212> TYPE: PRT
<213> ORGANISM: Artificial Sequence
<220> FEATURE:
<223> OTHER INFORMATION: fp-4

<400> SEQUENCE: 6

Tyr Gly Arg Arg Tyr Gly Glu Pro Ser Gly Tyr Ala Asn Ile Gly His
1               5                   10                  15

Arg Arg Tyr Tyr Glu Arg Ala Ile Ser Phe His Arg His Ser His Val
            20                  25                  30

His Gly His His Leu Leu His Arg His Val His Arg His Ser Val Leu
        35                  40                  45

His Gly His Val His Met His Arg Val Ser His Arg Ile Met His Arg
    50                  55                  60

His Arg Val Leu His Gly His Val His Arg His Val Leu His Asn
65                  70                  75                  80

His Val His Arg His Ser Val Leu His Gly His Val His Arg His Arg
                85                  90                  95

Val Leu His Arg His Val His Arg His Asn Val Leu His Gly His Val
            100                 105                 110

His Arg His Arg Val Leu His Lys His Val His Asn His Arg Val Leu
        115                 120                 125

His Lys His Leu His Lys His Gln Val Leu His Gly His Val His Arg
    130                 135                 140

His Gln Val Leu His Lys His Val His Asn His Arg Val Leu His Lys
145                 150                 155                 160

His Leu His Lys His Gln Val Leu His Gly His Val His Thr His Arg
                165                 170                 175

Val Leu His Lys His Val His Lys His Arg Val Leu His Lys His Leu
            180                 185                 190

His Lys His Gln Val Leu His Gly His Ile His Thr His Arg Val Leu
        195                 200                 205

His Lys His Leu His Lys His Gln Val Leu His Gly His Val His Thr
    210                 215                 220

His Arg Val Leu His Lys His Val His Lys His Arg Val Leu His Lys
225                 230                 235                 240

His Leu His Lys His Gln Val Leu His Gly His Val His Met His Arg
                245                 250                 255

Val Leu His Lys His Val His Lys His Arg Val Leu His Lys His Val
            260                 265                 270

His Lys His His Val Val His Lys His Val Ser His Arg Val Leu
        275                 280                 285

His Lys His Val His Lys His Arg Val Glu His Gln His Val His Lys
    290                 295                 300

His His Val Leu His Arg His Val His Ser His Val Val His Ser
305                 310                 315                 320

His Val His Lys His Arg Val Val His Ser His Val His Lys His Asn
                325                 330                 335

Val Val His Ser His Val His Arg His Gln Ile Leu His Arg His Val
            340                 345                 350

His Arg His Gln Val Val His Arg His Val His Arg His Leu Ile Ala
        355                 360                 365

His Arg His Ile His Ser His Gln Ala Ala Val His Arg His Val His
        370                 375                 380

Thr His Phe Glu Gly Asn Phe Asn Asp Asp Gly Thr Asp Val Asn Leu
385                 390                 395                 400

Arg Ile Arg His Gly Ile Ile Tyr Phe Gly Asn Thr Tyr Arg Leu
                405                 410                 415

Ser Gly Gly Arg Arg Phe Met Thr Leu Trp Gln Glu Cys Leu Glu
                420                 425                 430

Ser Tyr Gly Asp Ser Asp Glu Cys Phe Val Gln Leu Leu Glu Gly Asn
                435                 440                 445

Gln His Leu Phe Thr Val Val Gln Gly His His Ser Thr Ser Phe Arg
        450                 455                 460

Ser Asp Leu Ser Asn Asp Leu His Pro Asp Asn Asn Ile Glu Gln Ile
465                 470                 475                 480

Ala Asn Asp His Val Asn Asp Ile Ala Gln Ser Thr Asp Gly Asp Ile
                485                 490                 495

Asn Asp Phe Ala Asp Thr His Tyr Asn Asp Val Ala Pro Ile Ala Asp
                500                 505                 510

Val His Val Asp Asn Ile Ala Gln Thr Ala Asp Asn His Val Lys Asn
    515                 520                 525

Ile Ala Gln Thr Ala His His Val Asn Asp Val Ala Gln Ile Ala
    530                 535                 540

Asp Asp His Val Asn Asp Ile Gly Gln Thr Ala Tyr Asp His Val Asn
545                 550                 555                 560

Asn Ile Gly Gln Thr Ala Asp Asp His Val Asn Asp Ile Ala Gln Thr
                565                 570                 575

Ala Asp Asp His Val Asn Ala Ile Ala Gln Thr Ala Asp Asp His Val
                580                 585                 590

Asn Ala Ile Ala Gln Thr Ala Asp Asp His Val Asn Asp Ile Gly Asp
                595                 600                 605

Thr Ala Asn Ser His Ile Val Arg Val Gln Gly Val Ala Lys Asn His
        610                 615                 620

Leu Tyr Gly Ile Asn Lys Ala Ile Gly Lys His Ile Gln His Leu Lys
625                 630                 635                 640

Asp Val Ser Asn Arg His Ile Glu Lys Leu Asn Asn His Ala Thr Lys
                645                 650                 655

Asn Leu Leu Gln Ser Ala Leu Gln His Lys Gln Thr Ile Glu Arg
                660                 665                 670

Glu Ile Gln His Lys Arg His Leu Ser Glu Lys Glu Asp Ile Asn Leu
        675                 680                 685

Gln His Glu Asn Ala Met Lys Ser Lys Val Ser Tyr Asp Gly Pro Val
        690                 695                 700

Phe Asn Glu Lys Val Ser Val Val Ser Asn Gln Gly Ser Tyr Asn Glu
705                 710                 715                 720

Lys Val Pro Val Leu Ser Asn Gly Gly Tyr Asn Gly Lys Val Ser
                725                 730                 735

Ala Leu Ser Asp Gln Gly Ser Tyr Asn Glu Gly Tyr Ala Tyr
                740                 745                 750

<210> SEQ ID NO 7
<211> LENGTH: 82

-continued

```
<212> TYPE: PRT
<213> ORGANISM: Artificial Sequence
<220> FEATURE:
<223> OTHER INFORMATION: fp-5

<400> SEQUENCE: 7

Lys His His His His His Ser Ser Glu Glu Tyr Lys Gly Gly Tyr
1               5                   10                  15

Tyr Pro Gly Asn Thr Tyr His Tyr His Ser Gly Gly Ser Tyr His Gly
            20                  25                  30

Ser Gly Tyr His Gly Gly Tyr Lys Gly Lys Tyr Tyr Gly Lys Ala Lys
        35                  40                  45

Lys Tyr Tyr Tyr Lys Tyr Lys Asn Ser Gly Lys Tyr Lys Tyr Leu Lys
    50                  55                  60

Lys Ala Arg Lys Tyr His Arg Lys Gly Tyr Lys Lys Tyr Tyr Gly Gly
65                  70                  75                  80

Ser Ser

<210> SEQ ID NO 8
<211> LENGTH: 103
<212> TYPE: PRT
<213> ORGANISM: Artificial Sequence
<220> FEATURE:
<223> OTHER INFORMATION: fp-6

<400> SEQUENCE: 8

Ile Ala Ala Leu Cys Gly Ile Val Lys Ser Ile Asp Ser Asp Asp Ser
1               5                   10                  15

Asp Tyr Asp Tyr Lys Gly Arg Gly Tyr Cys Thr Asn Lys Gly Cys Arg
            20                  25                  30

Ser Gly Tyr Asn Tyr Phe Gly Asn Lys Gly Tyr Cys Lys Tyr Gly Glu
        35                  40                  45

Lys Ser Tyr Thr Tyr Asn Cys Asn Ser Tyr Ala Gly Cys Cys Leu Pro
    50                  55                  60

Arg Asn Pro Tyr Gly Lys Leu Lys Tyr Tyr Cys Thr Asn Lys Tyr Gly
65                  70                  75                  80

Cys Pro Asn Asn Tyr Tyr Phe Tyr Asn Asn Lys Gly Tyr Tyr Tyr Leu
                85                  90                  95

Glu His His His His His His
            100

<210> SEQ ID NO 9
<211> LENGTH: 199
<212> TYPE: PRT
<213> ORGANISM: Artificial Sequence
<220> FEATURE:
<223> OTHER INFORMATION: fp-151

<400> SEQUENCE: 9

Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
            20                  25                  30

Pro Ser Tyr Pro Pro Thr Tyr Lys Ala Lys Pro Ser Tyr Pro Pro Thr
        35                  40                  45

Tyr Lys Ala Lys Pro Ser Tyr Pro Pro Thr Tyr Lys Pro Trp Ser Ser
    50                  55                  60

Glu Glu Tyr Lys Gly Gly Tyr Tyr Pro Gly Asn Thr Tyr His Tyr His
65                  70                  75                  80
```

```
Ser Gly Gly Ser Tyr His Gly Ser Gly Tyr His Gly Tyr Lys Gly
                85                  90                  95

Lys Tyr Tyr Gly Lys Ala Lys Lys Tyr Tyr Lys Tyr Lys Asn Ser
            100                 105                 110

Gly Lys Tyr Lys Tyr Leu Lys Lys Ala Arg Lys Tyr His Arg Lys Gly
            115                 120                 125

Tyr Lys Lys Tyr Gly Gly Gly Ser Ser Ala Lys Pro Ser Tyr Pro
    130                 135                 140

Pro Thr Tyr Lys Ala Lys Pro Ser Tyr Pro Pro Thr Tyr Lys Ala Lys
145                 150                 155                 160

Pro Ser Tyr Pro Pro Thr Tyr Lys Ala Lys Pro Ser Tyr Pro Pro Thr
            165                 170                 175

Tyr Lys Ala Lys Pro Ser Tyr Pro Pro Thr Tyr Lys Ala Lys Pro Ser
            180                 185                 190

Tyr Pro Pro Thr Tyr Lys Leu
            195
```

<210> SEQ ID NO 10
<211> LENGTH: 171
<212> TYPE: PRT
<213> ORGANISM: Artificial Sequence
<220> FEATURE:
<223> OTHER INFORMATION: fp-131

<400> SEQUENCE: 10

```
Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
            20                  25                  30

Pro Ser Tyr Pro Pro Thr Tyr Lys Ala Lys Pro Ser Tyr Pro Pro Thr
            35                  40                  45

Tyr Lys Ala Lys Pro Ser Tyr Pro Pro Thr Tyr Lys Pro Trp Ala Asp
    50                  55                  60

Tyr Tyr Gly Pro Lys Tyr Gly Pro Pro Arg Arg Tyr Gly Gly Gly Asn
65                  70                  75                  80

Tyr Asn Arg Tyr Gly Arg Arg Tyr Gly Gly Tyr Lys Gly Trp Asn Asn
            85                  90                  95

Gly Trp Lys Arg Gly Arg Trp Gly Arg Lys Tyr Tyr Gly Ser Ala Lys
            100                 105                 110

Pro Ser Tyr Pro Pro Thr Tyr Lys Ala Lys Pro Ser Tyr Pro Pro Thr
            115                 120                 125

Tyr Lys Ala Lys Pro Ser Tyr Pro Pro Thr Tyr Lys Ala Lys Pro Ser
    130                 135                 140

Tyr Pro Pro Thr Tyr Lys Ala Lys Pro Ser Tyr Pro Pro Thr Tyr Lys
145                 150                 155                 160

Ala Lys Pro Ser Tyr Pro Pro Thr Tyr Lys Leu
            165                 170
```

<210> SEQ ID NO 11
<211> LENGTH: 175
<212> TYPE: PRT
<213> ORGANISM: Artificial Sequence
<220> FEATURE:
<223> OTHER INFORMATION: fp-353

<400> SEQUENCE: 11

```
Pro Trp Ala Asp Tyr Tyr Gly Pro Lys Tyr Gly Pro Pro Arg Arg Tyr
```

```
              1               5                  10                 15
Gly Gly Gly Asn Tyr Asn Arg Tyr Gly Arg Arg Tyr Gly Gly Tyr Lys
                20                 25                 30

Gly Trp Asn Asn Gly Trp Lys Arg Gly Arg Trp Gly Arg Lys Tyr Tyr
                35                 40                 45

Pro Trp Ser Ser Glu Glu Tyr Lys Gly Gly Tyr Tyr Pro Gly Asn Thr
         50                 55                 60

Tyr His Tyr His Ser Gly Gly Ser Tyr His Gly Ser Gly Tyr His Gly
65                  70                 75                 80

Gly Tyr Lys Gly Lys Tyr Tyr Gly Lys Ala Lys Lys Tyr Tyr Tyr Lys
                85                 90                 95

Tyr Lys Asn Ser Gly Lys Tyr Lys Tyr Leu Lys Lys Ala Arg Lys Tyr
                100                105                110

His Arg Lys Gly Tyr Lys Lys Tyr Tyr Gly Gly Ser Ser Gly Ser Ala
                115                120                125

Asp Tyr Tyr Gly Pro Lys Tyr Gly Pro Pro Arg Arg Tyr Gly Gly
        130                135                140

Asn Tyr Asn Arg Tyr Gly Arg Arg Tyr Gly Tyr Lys Gly Trp Asn
145                 150                155                160

Asn Gly Trp Lys Arg Gly Arg Trp Gly Arg Lys Tyr Tyr Gly Ser
                165                170                175
```

<210> SEQ ID NO 12
<211> LENGTH: 187
<212> TYPE: PRT
<213> ORGANISM: Artificial Sequence
<220> FEATURE:
<223> OTHER INFORMATION: fp-153

<400> SEQUENCE: 12

```
Ala Lys Pro Ser Tyr Pro Pro Thr Tyr Lys Ala Lys Pro Ser Tyr Pro
1               5                  10                 15

Pro Thr Tyr Lys Ala Lys Pro Ser Tyr Pro Pro Thr Tyr Lys Ala Lys
                20                 25                 30

Pro Ser Tyr Pro Pro Thr Tyr Lys Ala Lys Pro Ser Tyr Pro Pro Thr
                35                 40                 45

Tyr Lys Ala Lys Pro Ser Tyr Pro Pro Thr Tyr Lys Pro Trp Ser Ser
        50                 55                 60

Glu Glu Tyr Lys Gly Gly Tyr Tyr Pro Gly Asn Thr Tyr His Tyr His
65                  70                 75                 80

Ser Gly Gly Ser Tyr His Gly Ser Gly Tyr His Gly Tyr Lys Gly
                85                 90                 95

Lys Tyr Tyr Gly Lys Ala Lys Lys Tyr Tyr Lys Tyr Lys Asn Ser
                100                105                110

Gly Lys Tyr Lys Tyr Leu Lys Lys Ala Arg Lys Tyr His Arg Lys Gly
        115                120                125

Tyr Lys Lys Tyr Tyr Gly Gly Ser Ser Gly Ser Ala Asp Tyr Tyr Gly
130                 135                140

Pro Lys Tyr Gly Pro Pro Arg Arg Tyr Gly Gly Asn Tyr Asn Arg
145                 150                155                160

Tyr Gly Arg Arg Tyr Gly Gly Tyr Lys Gly Trp Asn Asn Gly Trp Lys
                165                170                175

Arg Gly Arg Trp Gly Arg Lys Tyr Tyr Gly Ser
                180                185
```

<210> SEQ ID NO 13
<211> LENGTH: 561
<212> TYPE: PRT
<213> ORGANISM: Artificial Sequence
<220> FEATURE:
<223> OTHER INFORMATION: fp-351

<400> SEQUENCE: 13

```
Pro Arg Ala Thr Arg Pro Ala Leu Ala Ala Ser Pro Thr Tyr Arg Thr
1               5                   10                  15

Tyr Arg Gly Leu Tyr Pro Arg Ala Leu Tyr Ser Thr Tyr Arg Gly Leu
            20                  25                  30

Tyr Pro Arg Ala Pro Arg Ala Ala Arg Gly Ala Arg Gly Thr Tyr Arg
        35                  40                  45

Gly Leu Tyr Gly Leu Tyr Gly Leu Tyr Ala Ser Asn Thr Tyr Arg Ala
    50                  55                  60

Ser Asn Ala Arg Gly Thr Tyr Arg Gly Leu Tyr Ala Arg Gly Ala Arg
65                  70                  75                  80

Gly Thr Tyr Arg Gly Leu Tyr Gly Leu Tyr Thr Tyr Arg Leu Tyr Ser
                85                  90                  95

Gly Leu Tyr Thr Arg Pro Ala Ser Asn Ala Ser Asn Gly Leu Tyr Thr
            100                 105                 110

Arg Pro Leu Tyr Ser Ala Arg Gly Leu Tyr Ala Arg Gly Thr Arg
        115                 120                 125

Pro Gly Leu Tyr Ala Arg Gly Leu Tyr Ser Thr Tyr Arg Thr Tyr Arg
    130                 135                 140

Pro Arg Ala Thr Arg Pro Ser Glu Arg Ser Glu Arg Gly Leu Ala Gly
145                 150                 155                 160

Leu Ala Thr Tyr Arg Leu Tyr Ser Gly Leu Tyr Gly Leu Tyr Thr Tyr
                165                 170                 175

Arg Thr Tyr Arg Pro Arg Ala Gly Leu Tyr Ala Ser Asn Thr His Arg
            180                 185                 190

Thr Tyr Arg His Ile Ser Thr Tyr Arg His Ile Ser Glu Arg Gly
        195                 200                 205

Leu Tyr Gly Leu Tyr Ser Glu Arg Thr Tyr Arg His Ile Ser Gly Leu
    210                 215                 220

Tyr Ser Glu Arg Gly Leu Tyr Thr Tyr Arg His Ile Ser Gly Leu Tyr
225                 230                 235                 240

Gly Leu Tyr Thr Tyr Arg Leu Tyr Ser Gly Leu Tyr Leu Tyr Ser Thr
                245                 250                 255

Tyr Arg Thr Tyr Arg Gly Leu Tyr Leu Tyr Ser Ala Leu Ala Leu Tyr
            260                 265                 270

Ser Leu Tyr Ser Thr Tyr Arg Thr Tyr Arg Thr Tyr Arg Leu Tyr Ser
        275                 280                 285

Thr Tyr Arg Leu Tyr Ser Ala Ser Asn Ser Glu Arg Gly Leu Tyr Leu
    290                 295                 300

Tyr Ser Thr Tyr Arg Leu Tyr Ser Thr Tyr Arg Leu Glu Ala Leu Tyr
305                 310                 315                 320

Ser Leu Tyr Ser Ala Leu Ala Ala Arg Gly Leu Tyr Ser Thr Tyr Arg
                325                 330                 335

His Ile Ser Ala Arg Gly Leu Tyr Gly Leu Tyr Thr Tyr Arg Leu
            340                 345                 350

Tyr Ser Leu Tyr Ser Thr Tyr Arg Thr Tyr Arg Gly Leu Tyr Gly Leu
        355                 360                 365

Tyr Ser Glu Arg Ser Glu Arg Gly Leu Tyr Ser Glu Arg Ala Leu Ala
```

```
                370                 375                 380
Leu Tyr Ser Pro Arg Ala Ser Glu Arg Thr Tyr Arg Pro Arg Ala Pro
385                 390                 395                 400

Arg Ala Thr His Arg Thr Tyr Arg Leu Tyr Ser Ala Leu Ala Leu Tyr
                405                 410                 415

Ser Pro Arg Ala Ser Glu Arg Thr Tyr Arg Pro Arg Ala Pro Arg Ala
                420                 425                 430

Thr His Arg Thr Tyr Arg Leu Tyr Ser Ala Leu Ala Leu Tyr Ser Pro
                435                 440                 445

Arg Ala Ser Glu Arg Thr Tyr Arg Pro Arg Ala Pro Arg Ala Thr His
                450                 455                 460

Arg Thr Tyr Arg Leu Tyr Ser Ala Leu Ala Leu Tyr Ser Pro Arg Ala
465                 470                 475                 480

Ser Glu Arg Thr Tyr Arg Pro Arg Ala Pro Arg Ala Thr His Arg Thr
                485                 490                 495

Tyr Arg Leu Tyr Ser Ala Leu Ala Leu Tyr Ser Pro Arg Ala Ser Glu
                500                 505                 510

Arg Thr Tyr Arg Pro Arg Ala Pro Arg Ala Thr His Arg Thr Tyr Arg
                515                 520                 525

Leu Tyr Ser Ala Leu Ala Leu Tyr Ser Pro Arg Ala Ser Glu Arg Thr
                530                 535                 540

Tyr Arg Pro Arg Ala Pro Arg Ala Thr His Arg Thr Tyr Arg Leu Tyr
545                 550                 555                 560

Ser

<210> SEQ ID NO 14
<211> LENGTH: 60
<212> TYPE: PRT
<213> ORGANISM: Artificial Sequence
<220> FEATURE:
<223> OTHER INFORMATION: fp-1 variant

<400> SEQUENCE: 14

Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
                20                  25                  30

Pro Ser Tyr Pro Pro Thr Tyr Lys Ala Lys Pro Ser Tyr Pro Pro Thr
                35                  40                  45

Tyr Lys Ala Lys Pro Ser Tyr Pro Pro Thr Tyr Lys
    50                  55                  60

<210> SEQ ID NO 15
<211> LENGTH: 196
<212> TYPE: PRT
<213> ORGANISM: Artificial Sequence
<220> FEATURE:
<223> OTHER INFORMATION: fp-151 variant

<400> SEQUENCE: 15

Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
                20                  25                  30

Pro Ser Tyr Pro Pro Thr Tyr Lys Ala Lys Pro Ser Tyr Pro Pro Thr
                35                  40                  45

Tyr Lys Ala Lys Pro Ser Tyr Pro Pro Thr Tyr Lys Ser Ser Glu Glu
```

```
                    50                  55                  60
Tyr Lys Gly Gly Tyr Tyr Pro Gly Asn Thr Tyr His Tyr His Ser Gly
 65                  70                  75                  80

Gly Ser Tyr His Gly Ser Gly Tyr His Gly Gly Tyr Lys Gly Lys Tyr
                 85                  90                  95

Tyr Gly Lys Ala Lys Lys Tyr Tyr Lys Tyr Lys Asn Ser Gly Lys
                100                 105                 110

Tyr Lys Tyr Leu Lys Lys Ala Arg Lys Tyr His Arg Lys Gly Tyr Lys
                115                 120                 125

Lys Tyr Tyr Gly Gly Gly Ser Ser Ala Lys Pro Ser Tyr Pro Pro Thr
            130                 135                 140

Tyr Lys Ala Lys Pro Ser Tyr Pro Pro Thr Tyr Lys Ala Lys Pro Ser
145                 150                 155                 160

Tyr Pro Pro Thr Tyr Lys Ala Lys Pro Ser Tyr Pro Pro Thr Tyr Lys
                165                 170                 175

Ala Lys Pro Ser Tyr Pro Pro Thr Tyr Lys Ala Lys Pro Ser Tyr Pro
                180                 185                 190

Pro Thr Tyr Lys
            195

<210> SEQ ID NO 16
<211> LENGTH: 76
<212> TYPE: PRT
<213> ORGANISM: Artificial Sequence
<220> FEATURE:
<223> OTHER INFORMATION: mgfp-5

<400> SEQUENCE: 16

Ser Ser Glu Glu Tyr Lys Gly Gly Tyr Tyr Pro Gly Asn Thr Tyr His
 1               5                  10                  15

Tyr His Ser Gly Gly Ser Tyr His Gly Ser Gly Tyr His Gly Gly Tyr
                20                  25                  30

Lys Gly Lys Tyr Tyr Gly Lys Ala Lys Lys Tyr Tyr Tyr Lys Tyr Lys
                35                  40                  45

Asn Ser Gly Lys Tyr Lys Tyr Leu Lys Lys Ala Arg Lys Tyr His Arg
             50                  55                  60

Lys Gly Tyr Lys Lys Tyr Tyr Gly Gly Gly Ser Ser
 65                  70                  75
```